United States Patent [19]

Bishai et al.

[11] Patent Number: 5,700,925
[45] Date of Patent: Dec. 23, 1997

[54] **DNA ENCODING STATIONARY PHASE, STRESS RESPONSE SIGMA FACTOR FROM *MYCOBACTERIUM TUBERCULOSIS***

[75] Inventors: William R. Bishai, Baltimore, Md.; Douglas B. Young, London, United Kingdom; Ying Zhang, Baltimore, Md.; James DeMaio, Tacoma, Wash.

[73] Assignee: The Johns Hopkins University, Baltimore, Md.

[21] Appl. No.: 622,353

[22] Filed: Mar. 27, 1996

[51] Int. Cl.$^6$ .................. C07H 21/02; C07H 21/04; C12N 9/00
[52] U.S. Cl. .................. 536/23.1; 435/183; 536/23.2; 536/23.4; 536/23.7
[58] Field of Search .................. 435/183; 536/23.1, 536/23.2, 23.4, 23.7

[56] References Cited

PUBLICATIONS

Smith et al., "Epidemioilogy of Tuberculosis," In R. Bloom (ed.), Tuberculosis: Pathogenesis, Protection, and Control, ASM Press, Washington, D.C., pp. 47–59.
Bloom et al., "Tuberculosis: Commentary on a Reemergent Killer," *Science*, 257:1055–1064 (1992).
Gedde–Dahl, "Tuberculosis Infection in the Light of Tuberculin Matriculation," *Am. J. Hyg.* 56:139–214 (1952).
Sudre et al., "Tuberculosis: A Global Overview of the Situation Today," *Bull Who* 70:149–159 (1992).
Wayne, "Dormancy of *Mycobacterium tuberculosis* and Latency of Disease," *Eur. J. Clin. Microbiol. Infec. Disc.*, 13:908–914.
Werner, "Filterable Forms of *Mycobacterium tuberculosis*," *Am. Rev. Tuberc.*, 69:473–474 (1953).
Ausubel et al., "Current Protocols in Molecular Biology" (John Wiley & Sons, Inc.), pp. 1.8.4–1.8.8 (1994).
Sambrook et al., Molecular Cloning: A Laboratory Manual (Cold Spring Harbor Lab. Press, Planview, NY), pp. 9.31–9.57 (1989).
Wayne, *Am. Rev. Resp. Dis.*, 114:807–811.
Firestein et al., *Anal. Biochem*, 167:381–386 (1987).
Lonetto et al., *J. Bacteriol.*, 174:3843–3849 (1992).
Gross et al., in Transcriptional Regulation, eds. McKnight et al. (Cold Spring Habor Lab. Press, Plainview, NY), 1:129–176 (1992).
Predich et al., *Mol. Microbiol.*, 15:355–366 (1995).
Kempsell et al., *Gen Microbiol*, 138:1717–1727 (1992).
Honore et al., *Mol. Microbiol*, 7:207–214 (1993).
Tanaka et al., *Science*, 242:1040–1042 (1988).
Potuckova et al., *Mol. Microbiol*, 17:37–48 (1995).
Gholamhoseinian et al., *J. Bacteriol*, 171:5747–5749 (1989).
Margolis et al., *Science*, 254:562–565 (1991).
Benson et al., *J. Bacteriol.*, 175:2347–2356 (1993).
Moran, "Measuring Gene Expression in Bacillus", In Molecular Biological Methods for Bacillus, C.R. Harwood and Cutting (ed.) Wiley & Sons, Chichester, England, pp. 267–293.

Lonetto et al., *PNAS*, 91:7573–7577 (1994).
Haines et al., *Biotechniques*, 12:736–740 (1992).
Spiegelman et al., "Purification of RNA Polymerase from Phage SP82–Infected *Bacillus subtillis*," *J. Biol. Chem.*, 249:1476–1482 (1974).
Benson et al., *PNAS*, 90:2330–2334 (1993).
Schmidt et al., *PNAS*, 87:9221–9225 (1990).
Alper et al., *Cell*, 77:195–205 (1994).
Schuler et al., *Proteins Struct. Funct. Genet.*, 9:180–190 (1991).
Stanford et al., *Tubercle*, 68:241–242 (1987).
Csillag et al., "The Mycococcus form of Mycobacteria," *J. Gen. Microbiol*, 34:341 (1964).
Khomenko, "The Variability of *Mycobacterium tuberculosis* in Patients with Cavitary Pulmonary Tuberculosis in the Course of Chemotherapy," *Tubercle*, 68:243–253 (1987).
Barksdale et al., "Spheroidal Bodies and Globi of Human Leprosy," *Biochem. Biophys Res. Comm.*, 54:290 (1973).
Chatterjee "A Non–Acid Fast Coccoid Precursor—Possible Cultivable Phase of *Mycobacterium leprae*", *Leprosy in India*, 48:398 (1976).
Rook et al., "Autoimmunity or Slow Bacterial Infection?" *Immunol. Today*, 13;160–164 (1992).
Fidler et al., "*Mycobacterium tuberculosis* DNA in Tissue Affected by Sarcoidosis," *BMJ* 306:546–549 (1993).
Haldenwang, *Microbiol. Rev.*, 59:1–30 (1995).
Dufour et al., "Interactions Between a *Bacillus subtillis* Anti–σ Factor (RsbW) and its Antagonists (RsbV)", *J. Bacteriol*, 176:1813–1820 (1994).
Kalman et al., "Similar Organization of the SigB and spoIIA Operons Encoding Alternative Sigma Factors of *Bacillus subtilis* RNA Polymerase," *J. Bacteriol.*, 172:5575–5585 (1990).
Min et al., "$\sigma^F$, The First Compartment–Specific Transcription Factor of *Bacillus subtilis*, is Regulated by an Anti–Sigma Factor Which is also a Protein Kinase," *Cell*, 74:735–742 (1993).
Stock et al., "Protein Phosphorylation and Regulation of Adaptive Responses in Bacteria," *Microbiol. Rev.*, 53:450–490 (1989).
Boylan et al., "Transcrition Factor $\sigma_B$, of *Bacillus subtilis* Controls a Large Stationary–Phase Regulon," *J. Bacteriol*, 175:3957–3963 (1993).
Burgess et al., "Purification of RNA Polymerase Sigma Factor," *Methods Enzymol*, 21:500–506 (1971).
Kumar et al., "An Improved Method for the Purification of DNA Dependent RNA Polymerase from *E. coli*," *J. Biochem Biophys. Methods*, 15:235–240 (1988).

*Primary Examiner*—James C. Housel
*Assistant Examiner*—Rodney P. Swartz
*Attorney, Agent, or Firm*—Cushman Darby & Cushmam IP Group of Pillsbury Madison & Sutro

[57] ABSTRACT

SigF is a gene that controls *M. tuberculosis* latency. A diagnostic test for latent tuberculosis involves detecting *M. tuberculosis* sigF in clinical specimens. A tuberculosis vaccine includes a *M. tuberculosis* strain with a mutation which disrupts the reading frame of its sigF gene.

6 Claims, 5 Drawing Sheets

FIG. IA
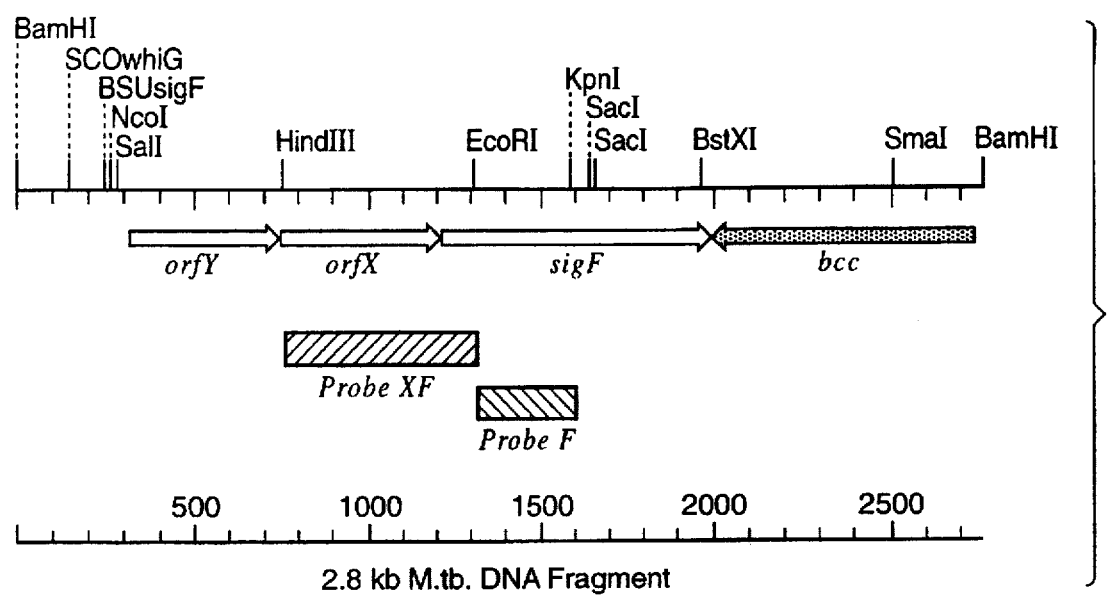
2.8 kb M.tb. DNA Fragment
FIG. IB
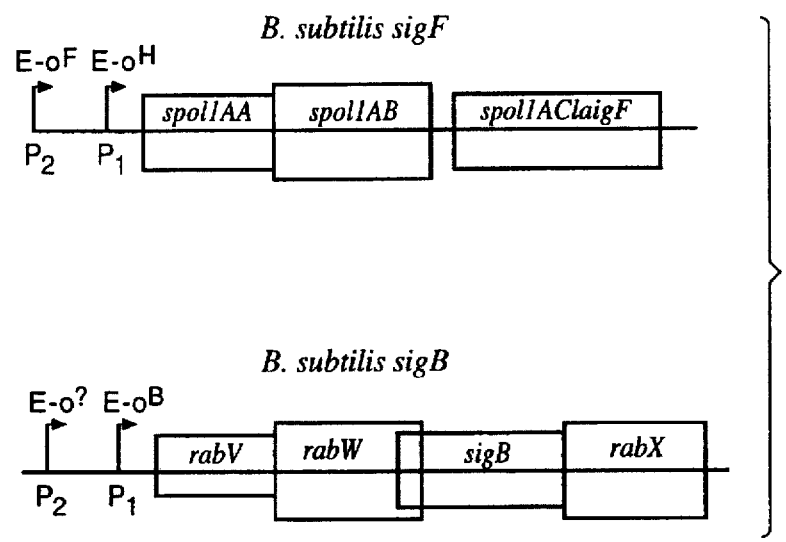

FIG. 2A

```
TCCAGACCTTCCACGACGGT CGCCAGCCCGATGTAGCCGG CAGTGTCTTCGGCATCACGT TGACCGCCCGACGGGCGCA
                                                                              80
                                                                          145/19
TCCAGCAG GTG ACG GCG CGC GCT GCC GGC GGT TCT GCA TCG CGA GCT AAC GAA TAC GCC GAC GTT
         M   T   A   R   A   A   G   G   S   A   S   R   A   N   E   Y   A   D   V>
                                                                              208/40
CCG GAG ATG TTT CGC GAG CTG GTT GGT TTG CCT GCC CTG TCA CCG GAA TTC CAG CGG CAC CGG
 P   E   M   F   R   E   L   V   G   L   P   A   L   S   P   E   F   Q   R   H   R>
                                                                              271/61
GAC AAG ATC GTT CAG CGG TGC TTG CCG CTG GCC GAT CAC ATC GCG CGG GTC AAC GCC GGT CGC
 D   K   I   V   Q   R   C   L   P   L   A   D   H   I   A   R   V   N   A   G   R>
                                                                              334/82
GGC GAA CCG CGT GAC GAC ATT CAG CGG GTC GAC TTC GTC GCG GTG CTG GGG GTT GAG TTC GAG
 G   E   P   R   D   D   I   Q   R   V   D   F   V   A   V   L   G   V   E   F   E>
                                                                              397/103
TTC GAC GTG AAG ACC TTC CGC GAC AAC AGC TGG TCG GTC AAG GTT CCT ACC ATC ATG GGC GTC
 F   D   V   K   T   F   R   D   N   S   W   S   V   K   V   P   T   I   M   G   V>
                                                                              460/124
CGA CGA CAC TTC CGC GAC GTC GAC AAC AGC GAT GCC CGG CGT CCC CGG CGT CTC AAG GAA CTG CAT
 R   R   H   F   R   D   V   D   N   S   D   A   R   R   P   R   R   L   K   E   L   H>
                                                                              523/145
CTG CGG CTA GGT ACC GCC ACC GCC GAT TTG TCG CAG CGG CTC GGG CGG GCG CCG TCG GCA TCG
 L   R   L   G   T   A   T   A   D   L   S   Q   R   L   G   R   A   P   S   A   S>
```

FIG. 2B

```
GAG CTC GCC GCG GAG CTC GGG ATG GAC CGC GCT GAG GTT ATC GAA GGT TTG CTG GCG GGT AGT
 E   L   A   A   E   L   G   M   D   R   A   E   V   I   E   G   L   L   A   G   S >
                                                                              586/166
                                                                                  649/187
TCC TAC CAC ACC TTG TCC ATC GAC AGC GAC GAC GAT GCC CGC GCA ATC ACA
 S   Y   H   T   L   S   I   D   S   D   D   D   A   R   A   I   T >
                                                                  712/208
GAC ACC CTG GGC GAT GTG GAT GCG GGT CTT GAC CAG ATC GAG AAT CGG GAG GTG CTT CGT CCG
 D   T   L   G   D   V   D   A   G   L   D   Q   I   E   N   R   E   V   L   R   P >
                                                                              775/229
TTG CTC GAG GCG CAG ATC GCC TTG CCC GAG CGG GAA ACG GTC TTG GTG CTC AGG TTC TTC GAC TCG ATG
 L   L   E   A   Q   I   A   L   P   E   R   E   T   V   L   V   L   R   F   F   D   S   M >
                                                                                      838/250
ACC CAA ACG CAG ATC GCC GAG CGC GTC GGT ATC TCA CAG ATG CAC GTG TCG CGG GTG GCC
 T   Q   T   Q   I   A   E   R   V   G   I   S   Q   M   H   V   S   R   V   A >
         261

AAG TCA TTG GCA CGG CTA CGG GAT CAG TTG GAG TAG  CCGCCGGGCTTACTTGGATCTC
 K   S   L   A   R   L   R   D   Q   L   E   *
                                           896
```

FIG. 3

```
MTBSIGF                   ............................MPREH      26
SCORPOF   mtaraagdsastanevadvpe......................Ga.....     50
BSUSIGF   mphstpqappappadqaqapaqeapapqrsrgadtralgqv..........    27
BSUSIGF   mdvevkknqKNAQLKDHEWKELIKQSQ......................       27
BSUSIGB   mqqp....SKTKLTKDEADRLISDYQ.......................       23

MTBSIGF   KD AP   HD V AAL AN   VRYA A  RS N M      GT           76
SCORPOF      ..NG-D qA  LI  N R VWS VQ  LN YEP      G

1

DNA ENCODING STATIONARY PHASE, STRESS RESPONSE SIGMA FACTOR FROM *MYCOBACTERIUM TUBERCULOSIS*

This invention was made using U.S. government grants from the National Institutes of Health AI36973 and AI07417. Therefore the U.S. government retains certain rights to the invention.

TECHNICAL FIELD OF THE INVENTION

The present invention is directed to a gene involved in latency of infection and a diagnostic method for detecting latent *M tuberculosis*. The present invention is also directed to *M. tuberculosis* vaccines having mutant sigF genes.

BACKGROUND OF THE INVENTION

Tuberculosis is the leading cause of death due to infection, causing an estimated 2.5 million deaths and 7.5 million cases per year worldwide (1). In the United States, rates of tuberculosis began to increase in 1985 after 40 years of steady decline. In addition, a number of American cities are reporting high rates of infection by multiply drug resistant tuberculosis. Such mycobacteria cause a high mortality rate because available antibiotics are ineffective (2).

About 90% of individuals who become infected with *M. tuberculosis* do not have immediate symptoms but develop a positive reaction to the tuberculin skin test and carry the bacteria in a dormant or latent state (3). Over a lifetime, these individuals have a 10% risk of developing reactivation tuberculosis in which, after years of quiescence, the tubercle bacilli resume growth and cause classic pulmonary tuberculosis as well as other forms of disease. One billion people, roughly one-third of the world's population, have latent tuberculosis (4). Individuals with latent tuberculosis currently require prolonged therapy because antimycobacterial drugs work poorly against dormant bacilli.

Little is known regarding the state of dormant tubercle bacilli within the human host (5). There is a controversial body of literature describing filterable forms, granular bacillary bodies, and L-forms associated with tubercle bacilli (6, 7). These forms were reported as early as 1907 when Hans Much described granular non-acid-fast bacilli in tuberculous abscesses (30). The granules, which came to be known as Much's granules, were filterable, failed to grow in culture, and failed to produce typical tuberculosis when inoculated into animals. However, if tissue from the first animal was inoculated into a second, classic tuberculosis ensued. Similar observations have been reported over the decades for both tuberculosis (31, 32) and leprosy (33, 34). Dormant or altered mycobacterial forms have also been proposed as etiologic agents for granulomatous diseases such as sarcoidosis and inflammatory bowel disease (35). There have been reports of PCR-amplifiable, mycobacterial DNA in the tissues of patients with these diseases (36).

Because latent tubercle bacilli survive for years and cannot be detected by acid-fast staining, the bacilli must be assumed to undergo significant morphologic changes during dormancy. Though these changes are poorly understood, they could involve expression of novel mycobacterial antigens which are not produced or cannot be recovered from bacteriologic cultures grown in vitro.

There is a need in the art for diagnostic and therapeutic methods for detecting, treating, and preventing latent tuberculosis.

SUMMARY OF THE INVENTION

It is an object of the invention to provide a DNA segment encoding a *M. tuberculosis* gene.

It is an object of the invention to provide a DNA segment encoding a *M. tuberculosis* sigma factor.

It is another object of the invention to provide a preparation of an isolated sigma factor from *M. tuberculosis*.

It is another object of the invention to provide a polypeptide which consists of a portion of a sigma factor of *M. tuberculosis*.

It is still another object of the invention to provide a fusion polypeptide of an *M. tuberculosis* sigma factor.

It is another object of the invention to provide a method for detecting the presence of a latent pathogenic mycobacterium in a human.

It is still another object of the invention to provide a tuberculosis vaccine strain.

These and other objects of the invention are provided by one or more of the embodiments described below. In one embodiment of the invention an isolated and purified subgenomic DNA segment is provided. Its nucleotide sequence is shown in SEQ ID NO: 1.

In another embodiment of the invention an isolated and purified subgenomic DNA segment encoding an *M. tuberculosis* sigma factor sigF as shown in SEQ ID NO: 2 is provided.

In another embodiment of the invention a preparation of an isolated sigma factor sigF from *M. tuberculosis* is provided. The amino acid sequence of the sigma factor is shown in SEQ ID NO:2.

In yet another embodiment of the invention a preparation which consists of a polypeptide is provided. The polypeptide is a sigma factor sigF from *M. tuberculosis* as shown in SEQ ID NO:2.

In another embodiment of the invention a preparation of an isolated polypeptide is provided which consists of at least four contiguous amino acids of the sequence shown in SEQ ID NO:2.

In still another embodiment of the invention a fusion polypeptide is provided. The polypeptide is the product of a genetic fusion of a first and second gene sequence, wherein the first sequence is an *M. tuberculosis* sigF gene and the second sequence encodes all or a portion of a second protein.

In another embodiment of the invention a method is provided of detecting the presence of a latent pathogenic mycobacterium in a human. The method comprises the steps of: detecting sigma factor sigF in a body sample isolated from a human, the presence of sigma factor sigF indicating a latent pathogenic mycobacterial infection in a human.

In another embodiment of the invention a tuberculosis vaccine is provided which comprises an *M. tuberculosis* strain with a mutation disrupting the reading frame of its sigF gene.

These and other embodiments of the invention provide the art with diagnostic, therapeutic and prophylactic reagents and methods for combatting latent tuberculosis.

BRIEF OF DESCRIPTION OF THE DRAWINGS

FIG. 1. Map of 2.8 kb *M. tuberculosis* DNA fragment containing sigF

FIG. 1A shows the restriction map and open reading frame analysis of the *M. tuberculosis* sigF gene cluster. The relative positions of restriction sites, the sigF open-reading frame, and the positions of promoter consensus sites for *Streptomyces coelicolor* WhiG (SCOwhiG) and *Bacillus subtilis* SigF (BSUsigF) are shown. Numbers along the bottom line are in bp.

FIG. 1B shows the genetic organization of the *B. subtilis* sigF and *B. subtilis* sigB gene clusters for comparison. Diagram shows that the arrangement anti-anti-sigma→anti-sigma→sigma is conserved since spoIIAA and rsbV encode anti-anti-sigma, and spoIIAB and rsbW encode anti-sigmas.

FIG. 2. DNA and deduced protein sequence of the *M. tuberculosis* sigF region

The 896 bp of *M. tuberculosis* DNA sequenced is shown in FIGS. 2A and 2B along with the deduced protein sequence of sigF. Numbers at right correspond to nucleotide/ amino acid positions.

FIG. 3. Alignment of *M. tuberculosis* sigF with related sigma factors

The deduced amino acid sequences of *M. tuberculosis* sigF aligned with homologues using the MACAW algorithm (29). Capitalized blocks of amino acids represent segments with statistically significant homology scores. Black and gray shading indicates amino acid similarity (black being the highest). The length of each polypeptide is shown by the numbers on the right. BSUsigF=*Bacillus subtilis* sigF (Acc. No. M15744, SEQ ID NO:8), BSUSIGB=*Bacillus subtilis* SigB (Acc. No. M13927, SEQ ID NO:9), and SCOsigF=*Streptomyces coelicolor* sigF (Acc. No. L11648, SEQ ID NO:7).

FIG. 4. RNase protection assay (RPA) with RNA extracts from *M. bovis* BCG exposed to different conditions.

Autoradiogram of RPA reaction products following liquid hybridization between total BCG RNA the pCK1845-derived sigF-specific antisense RNA probe separated on a 5% denaturing polyacrylamide gel and exposed to X-ray film for 24 hr. Samples B-H were assayed in duplicate. RPA was performed upon equivalent amounts of total RNA from *M. bovis* BCG cultures subjected to the following conditions: A, 10 mM $H_2O_2$; B, 5% EtOH; C, nitrogen depletion; D, cold shock; E, microaerophilic stress; F, early exponential growth ($A_{600}$=0.67); G, late exponential growth ($A_{600}$=1.5); H, stationary phase ($A_{600}$=2.7). Control samples were: I, an in vitro transcribed non-complementary probe (negative control); J, in vitro transcribed sense-strand sigF probe containing 350 complementary bases (positive control).

DETAILED DESCRIPTION OF THE INVENTION

Figure 4:
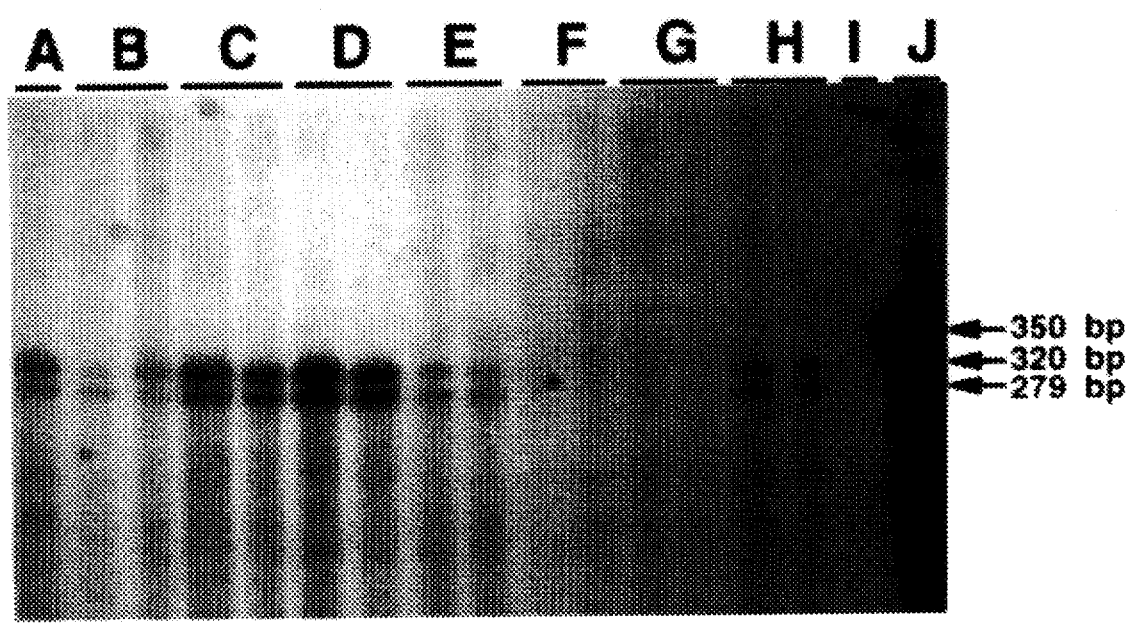

It is a discovery of the present invention that entry of *M. tuberculosis* into a latent state is under the influence of an *M. tuberculosis* gene encoding a sigma factor, sigF. The expression of *M. tuberculosis* gene sigF indicates the latent state of *M. tuberculosis*.

An *M. tuberculosis* sigF DNA segment can be isolated by amplifying sigma-like gene fragments from *M. tuberculosis* genomic DNA using polymerase chain reaction with degenerate primers. Primers are designed to anneal to conserved regions of bacterial sigma factors. PCR fragments which are generated are subsequently used to screen an *M. tuberculosis* genomic library. The clones which hybridize to the PCR fragments are analyzed by restriction enzyme digestion and compared to the sigma factors from other species, e.g., *M. smegmatis*. The clones which show strong homology to the sigma factors previously described from other mycobacteria are further analyzed by standard DNA sequencing methods. The sequence of one such genomic clone is 2.8 kb. As shown in SEQ ID NO: 1 the clone contains the *M. tuberculosis* sigma factor sigF gene. The sequence of the clone reveals a 261 codon open-reading frame (nucleotides 1250–2031 in SEQ ID NO: 1) encoding *M. tuberculosis* sigF protein as shown in SEQ ID NO:2. A subgenomic DNA segment consisting of the nucleotide sequence shown in SEQ ID NO: 1 or encoding an *M. tuberculosis* sigF protein as shown in SEQ ID NO:2 can be readily isolated and purified from a genomic clone or directly from *M. tuberculosis* genomic DNA. Any known methods for subgenomic DNA segment isolation, e.g., PCR, or restriction enzyme digestion, can be used employing the sequence information disclosed in SEQ ID NO: 1.

The DNA sequence provided herein can be used to form vectors which will replicate the sigF gene in a host cell. Vectors may comprise an expression control sequence and preferably express all or a part, of the *M. tuberculosis* sigF protein. Suitable vectors, for expression of proteins in both prokaryotic and eukaryotic cells, are known in the art. Some vectors are specifically designed to effect expression of inserted DNA segments downstream from a transcriptional and translational control site. Selection of a vector for a particular purpose may be made using knowledge of the properties and features of the vectors, such as useful expression control sequences. Vectors can be used to transform host cells. Methods of transformation are known in the art, and can be used according to suitability for a particular host cell. Host cells can be selected according to their known characteristics. Non-mycobacterial cells are particularly desirable.

DNA sequences which encode the same amino acid sequence as shown in SEQ ID NO:2 can also be used, e.g., for expressing sigF, without departing from the contemplated invention. Such sequences can be readily designed using the genetic code and its inherent degeneracy. Variations from the sequence shown in SEQ ID NO: 1 can be made, as is known in the art, employing alternate codon for the same amino acids, or employing alternate sequences in the non-coding region. A portion or all of the *M. tuberculosis* sigF gene can also be cloned in-frame with a second protein-coding sequence to make a fusion protein. A portion of the sigF gene can encode at least 4, 6, or 8 contiguous amino acids of the desired protein. Preferably the contiguous amino acids of sigF form an immunogen or an epitope. The second protein-coding sequence of the fusion protein may be all or a portion of a protein, e.g., glutathione-S-transferase (GST) or hemagglutinin (HA), which preferably is immunogenic and enhances the immune response to sigF protein. The second protein-coding sequence may encode at least 4, 6, or 8 contiguous amino acids of the protein. The product of the genetic fusion of the *M. tuberculosis* sigF gene, and the second protein is very useful in generating antibodies specifically immunoreactive to *M. tuberculosis* sigF protein.

*M. tuberculosis* sigF protein can be isolated from *M. tuberculosis* by any means known in the art for purifying proteins. For example, antibodies which specifically bind to sigF protein (see discussion below) can be employed for affinity purification. The procedures for protein purification are well known and routinely practiced in the art. A part of the sigF protein may be at least 4, 6, or 8 contiguous amino acids, which preferably forms an epitope. Such polypeptides are useful as immunogen or as competitive antigens. SigF proteins or polypeptides can be prepared and isolated substantially free of other mycobacterial proteins inter alia from transformed non-mycobacterial host cells expressing the protein or the polypeptide.

Clinical specimens can be tested for the presence of a dormant pathogenic mycobacterium including *M. tuberculosis*. The presence of *M. tuberculosis* sigF in a body sample indicates a latent pathogenic mycobacterial infection in a human. The clinical specimens can include samples obtained from biopsies, blood, and body discharge such as sputum, gastric content, spinal fluid, urine, and the like.

Mycobacterial RNA or protein of the specimen may be isolated directly from the specimen using any procedure known in the art.

The presence of M. tuberculosis sigF RNA may be detected by Northern blot, RNAse protection assay, primer extension, RT-PCR, or any other method known in the art. The probes and primers used in these methods can be designed based on the sequence disclosed in SEQ ID NO:1; this is well within the ability of persons of ordinary skill in the art. The probes for Northern blot and RNAse protection assay may be at least 20, 40, or 60 base pairs in length, preferably about 100 to 200 base pairs. The primers for RT-PCR and primer extension may be at least 10 base pairs in length and preferably about 20 base pairs. The probes and primers should be unique to M. tuberculosis sigF gene.

The presence of M. tuberculosis sigF protein can be detected by Western blot, sandwich assay, immunoprecipitation, or any techniques known in the art. Monoclonal or polyclonal antibodies raised using M. tuberculosis sigF protein or polypeptides as an immunogen can be used as probes in Western blot, can be bound to a solid support phase for sandwich assay, or can be used to immunoprecipitate radioactively labelled M. tuberculosis sigF protein.

An antibody preparation which is specifically immunoreactive with M. tuberculosis sigF protein can be obtained by standard techniques known in the art. Briefly, animals can be immunized with peptides along with adjuvants to generate polyclonal antibodies or hybridomas can be generated to obtain monoclonal antibodies. Antibodies may be polyclonal or monoclonal and may be raised using any protein containing M. tuberculosis sigF epitopes as an immunogen, including native M. tuberculosis sigF, M. tuberculosis sigF fusion proteins, or M. tuberculosis sigF peptides. The antibodies should be specifically immunoreactive with sigF epitopes. Preferably the selected epitopes will not be present on other mycobacterial or human proteins.

An M. tuberculosis strain can be constructed with a mutation, preferably one which disrupts the reading frame of the sigF gene. The mutation can be a deletion of part or all of a sigF gene. The sigF gene can also be disrupted by insertion or substitution mutations. Frame shift and nonsense mutations can also be employed. These mutations can be made by any means known in the art, e.g., PCR, restriction digestion, in vitro or in vivo mutagenesis. Such a strain with a dysfunctional sigF gene grows actively within a mammalian host for several weeks inducing a strong immune response, but because of the absence of a functional sigF protein, it is unable to establish a persistent infection. The host immune system is therefore able to clear the infection. Such a sigF mutant strain is useful as an anti-tuberculosis vaccine.

The following examples are provided for exemplification purposes only and are not intended to limit the scope of the invention.

Example 1

PCR with degenerate sigma-70 consensus primers successfully identifies an M. tuberculosis sigma factor gene, sigF Degenerate primers Y207 (5'-AACCTGCGHCTSGTSGTC-3' SEQ ID NO:3, a forward primer for the hexapeptide, NLRLVV SEQ ID NO: 4) and Y208 (5'-CTGNCGKATCCACCASGTSGCRTA-3' SEQ ID NO:5, a reverse primer for the octapeptide, YATWWIRQ SEQ ID NO:6) were used to amplify sigma factor gene fragments from M. tuberculosis genomic DNA in standard PCR reactions with Taq polymerase (Gibco-BRL, Gaithersburg, Md.): 30 cycles, 94° C. for 60 sec, 54° C. for 90 sec, and 72° C. for 120 sec. PCR products were cloned and used as probes to select genomic clones from an M. tuberculosis H37Rv cosmid library (kindly provided by K. de Smet). Analysis of bacterial sigma factors reveals considerable conservation in regions 2.1–2.4 and 4.1–4.2 (11). Region 2.1 is implicated in core polymerase-binding while the 2.3/2.4 and 4.2 regions are believed to contact the −10 and −35 regions, respectively, of the promoter DNA consensus sequence (12). We designed degenerate primers Y207 and Y208 directed towards conserved regions 2.1 and 2.3, respectively, and used them to amplify sigma-like gene fragments from M. tuberculosis genomic DNA. These primers amplified several distinct products including the anticipated 165 bp fragment. This 165 fragment was likely to consist of a mixture of sequences since it hybridized strongly to two separate M. tuberculosis BamHI fragments (4.8 kb and 2.8 kb) by Southern analysis. E. coli cosmid clones which hybridized with the 165 bp PCR product were selected by screening an M. tuberculosis H37Rv library, and the 2.8 kb BamHI fragment was subcloned as pYZ99 from one of these cosmids. A restriction map of the 2.8 kb BamHI fragment is shown in FIG. 1. The 4.8 kb BamHI fragment was identical to a 7 kb fragment from M. tuberculosis which had already been sequenced (S. Cole and L Smith, personal communication). This fragment also showed strong homology to one of the sigma factors previously described from M. smegmatis (13).

Sigma factors are subunits of bacterial RNA polymerase and confer promoter specificity to the holoenzyme complex. The unique affinity of each sigma factor for its promoter consensus sequence is an essential component in many gene regulation systems. For example, in Bacillus subtilis, sporulation is regulated by a carefully-coordinated cascade of alternate sigma factors and the genes which they control (37).

The structure and function of sigma factors are conserved across species, and these regions of conservation may be exploited to identify new sigma factors (16). We successfully employed PCR using degenerate primers based on conserved regions 2.1 and 2.3 to identify a new M. tuberculosis sigma factor gene, sigF.

Example 2

The sequence of the M. tuberculosis sigma factor gene, sigF DNA sequencing was performed with an Applied Biosystems 373 automated DNA sequencer (Foster City, Calif.) using dye terminator chemistry at the Biopolymer lab of the Howard Hughes Medical Institute at The Johns Hopkins University School of Medicine.

A combination of primer walking and subcloning of restriction fragments was used to determine the DNA sequence of 896 bp of pYZ99 which contains the sigma factor gene, sigF as shown in FIGS. 2A and 2B. Each base was sequenced an average of 5 times (minimum 3, maximum 8). The sequence reveals a 261 amino acid open-reading frame. The 88 bp of upstream sequence does not contain significant homology to E. coli sigma-70 promoter consensus sequences, nor does it have a clear-cut Shine-Dalgarno ribosome binding site with complementarity to the 3' end of the M. tuberculosis 16S rRNA sequence (14). Nevertheless, the sigF gene is clearly transcribed in slow-growing mycobacteria (see below). Our assignment of the initiation codon is based on alignments with other known sigF-like proteins (see below) and the observation that GTG is commonly used as an initiation codon in mycobacteria (15).

Example 3

Homologues of SigF

The 261 aa deduced protein encoded by *M. tuberculosis* sigF has significant homology to the known stress and sporulation-specific sigma factors from Bacillus spp. and Streptomyces spp. The closest similarities are to *S. coelicolor* SigF (41% identity and 62% similarity), *B. subtilis* SigB (30% identity and 50% similarity) and *B. subtilis* SigF (26% identity and 44% similarity). An alignment of the deduced *M. tuberculosis* SigF protein sequence with these three other sigma factors is shown in FIG. 3. In addition, a partial SigF homologue is present in *M. leprae* (Acc. No. U00012); frameshift sequencing errors in the *M. leprae* sigF sequence may explain the incompleteness of this open-reading frame.

*M. tuberculosis* SigF has closest homology to *S. coelicolor* SigF, *B. subtilis* SigF, and *B. subtilis* SigB. The *S. coelicolor* SigF gene encodes a late-stage, sporulation-specific sigma factor. *S. coelicolor* SigF knockout routants are unable to sporulate effectively producing deformed, thin-walled spores (17). *B. subtilis* SigF is essential for early spore gene expression. It is not transcribed until shortly after the start of sporulation (18), and its protein product is specifically activated within the developing forespore following septation (19). The *B. subtilis* SigB gene encodes a stress response sigma factor. While not an essential gene for growth or sporulation, SigB transcription is activated during stationary phase or under environmental stress, such as heat or alcohol shock (20, 21).

Lonetto et al. (11, 22) have divided the known sigma factors into a number of families based upon their primary structure homology patterns. The families include: primary sigma factors, a sporulation-specific group, a heat shock-related group, a flagellar-related group, and the newly recognized extracytoplasmic family. An important implication of these sequence homology clusters is that correlations between the primary structure and general function of bacterial sigma factors is preserved even across species barriers. The homology profile of *M. tuberculosis* SigF places it in the sporulation-specific family of such sigma factor classifications. This observation indicates that *M. tuberculosis* sigF has a functional role akin to those of the *S. coelicolor* and *B. subtilis* sigma factors to which it is similar.

Example 4

Other mycobacteria which contain sigF-like genes

Southern blots were made from PvuII digested, mycobacterial genomic DNA obtained from clinical isolates kindly provided by J. Dick. The blots were probed with a 221 base pair, *M. tuberculosis* -specific probe (base pairs 438 to 659) according to a previously published protocol (9). Hybridizations were performed overnight at 55° C. and were followed by five washes in 3xSSC at 45° C.

Southern blots of PvuII digested, mycobacterial, genomic DNA revealed sigF cross-hybridization in several slow-growing mycobacteria including *M. bovis* BCG (ATCC 35734) and clinical isolates of *M. avium, M. triviale*, and *M. gordonae*. The rapid growing species, *M. smegmatis* and *M. abscessus*, showed not hybridization by Southern blot analysis at intermediate stringency.

*M. tuberculosis* sigF-like sequences were identified by Southern blot analysis in several slow growing mycobacterial species including *M. bovis* BCG and *M. avium. M. leprae* was known prior to this study to possess a sigF homologue on cosmid B1308 (Acc. No. U00012). Rapid growing species, such as *M. smegmatis* and *M. abscessus*, showed no sigF hybridization by Southern blot. It is intriguing to postulate that the mycobacterial sigF gene might be associated with a developmental response unique to slow-growers. Alternatively, the absence of a sigF cross-hybridization in the rapidly growing species may simply be a function of increased evolutionary distance and decreased base pair homology.

Example 5

Stress and stationary phase induction of sigF mRNA

Strains and Plasmids pYZ99 is pUC18 containing a 2.8 kb BamHI fragment of *M. tuberculosis* genomic DNA. pCK1845 is pCRII (Invitrogen, San Diego, Calif.) containing a 279 bp EcoRI/KpnI subclone of the *M. tuberculosis* sigF gene with an SP6 promoter site and a BamHI site at the 5' end of the sigF gene fragment and a T7 promoter site and an EcoRV site at the 3' end. Recombinant plasmids were constructed and transformed into *E. coli* DH5 by electroporation using standard protocols (8), and they were isolated and purified using the Qiagen system (Qiagen, Inc., Chatsworth, Calif.).

Mycobacterial cultures

Early exponential, late-exponential, and stationary phase Bacille Calmette-Guerin (BCG, Pasteur strain, ATCC 35734) cultures were grown in standard Middlebrook 7H9 broth (Difco Laboratories, Detroit, Mich.) supplemented with ADC and Tween 80 (ADC-TW, ref. 11) at 37° C. with constant shaking. For cold shock, log phase cultures ($A_{600}$= 0.78) were placed at 4° C. for 24 hours prior to harvesting. To test other stress conditions, log-phase cultures were centrifuged and resuspended in a stress broth at 37° C. with shaking for 24 hours. Stress broths consisted of Middlebrook 7H9-ADC-TW plus 10 mM $H_2O_2$ (oxidative stress) or 5 % ethanol (alcohol stress). Nitrogen depleted medium was Middlebrook 7H9 containing only 10% of the standard amounts of glutamine and $NH_4Cl$. Microaerophilic cultures were prepared according to the settling method described by Wayne (10) for 7 days.

RNA Extraction and Quantification

Mycobacterial pellets were resuspended in extraction buffer (0.2M Tris, 0.5M NaCl, 0.01M EDTA, 1% SDS) plus an equal volume of phenol:chloroform:isoamyl alcohol (25:24:1). A 0.4 g aliquot of 300/μm prewashed glass beads (Sigma Chemical Company, St Louis, Mo.) was added and the samples were vortexed for 2 minutes at high speed. After a brief centrifugation, the aqueous phase was removed, re-extracted with phenol:chloroform:isoamyl alcohol, and finally extracted with chloroform:isoamyl alcohol (24: 1). The purified RNA was ethanol precipitated and quantified by $A_{260}$ measurement. Specific mRNA levels were determined by RNase protection assay (RPA, ref. 38) using a $^{32}$P-labeled, in vitro transcribed, sigF antisense RNA probe derived from BamH1-cut pCK1845 (Maxiscript system, Arabion, Austin, Tex.). Control, nonlabeled sigF sense RNA was produced using the same DNA template cut with EcoRV, transcribed in the opposite direction. For each assay equal quantities of total mycobacterial RNA were tested.

Transcription of sigF was detected and monitored under different growth conditions of BCG, a slow-growing attenuated *M. bovis* strain which is a member of the *M. tuberculosis* complex, using an RNase protection assay (RPA, see FIG. 4). Our ability to protect a $^{32}$P-labeled sigF antisense RNA probe using total RNA isolated from BCG using RPA analysis confirms that sigF is a transcribed gene in this close relative of *M. tuberculosis*. Replicate experiments showed that the RPA signal intensity results were reproducible to within 20% when performed with different batches of RNA on different days. The twin protected bands at 320 and 279 bases (FIG. 4) were observed consistently with the pCK1845-derived sigF antisense RNA probe. Secondary structure analysis of our probe reveals that about 40 bases of vector sequences at its 3' end are capable of forming a stem-loop which would protect a larger portion of the probe than the expected 279 bases. Both bands chase to 350 bases when a non-labeled, sense-strand RNA complementary over 350 bases is added. Hence we believe that both bands result from protection of the probe by sigF mRNA.

In BCG cultures, sigF transcription was most strongly induced during stationary phase ($A_{600}$=2.7), nitrogen depletion, and cold shock. A weak RPA signal was present during late-exponential phase ($A_{600}$=1.5), oxidative stress (10 mM $H_2O_2$), microaerophilic culture conditions, and alcohol shock (5% ethanol). No sigF mRNA was detected during early exponential phase growth ($A_{600}$=0.67). The relative intensities of the RPA signals during different growth conditions is summarized in Table 1.

TABLE 1 sigF RPA signal relative to baseline for BCG grown under different conditions

| Growth Condition | RPA Signal Intensity* (relative to baseline) |
|---|---|
| Early Exponential Phase ($A_{600}$ = 0.67) | 1.0 |
| Late Exponential Phase ($A_{600}$ = 1.5) | 3.6 |
| Stationary Phase ($A_{600}$ = 2.7) | 9.8 |
| Oxidative Stress (10 mM $H_2O_2$) | 4.8 |
| Alcohol Shock (5% ethanol) | 2.8 |
| Cold Shock (4° C.) | 17.6 |
| Nitrogen Depletion | 8.8 |
| Microaerophilic Stress | 3.2 |

*Equal amounts of total bacterial RNA (0.85 µg) were used in each assay. Duplicate or quadruplicate aliquots of each stress culture were processed independently and average values are shown above. Quantitation was performed by digitally photographing the autoradiogram on an Ambis camera and then analyzing the bands on the NIH Imager program. Baseline was defined as the signal intensity at 279–320 nt. of early exponential phase samples which was essentially the same as background.

RNase protection assays using an *M. tuberculosis* sigF-specific probe showed that the *M. tuberculosis* sigF open reading frame is a transcribed gene. Transcription was maximal during stationary phase, cold shock, and nitrogen depletion. Weaker RPA signals were present during other stress conditions, such as oxidative stress, alcohol shock, and microaerophilic stress. No evidence of transcription was seen during exponential-phase growth. RPA is highly sensitive and can detect mRNA at the femtogram level (23). These findings show that the *M. tuberculosis* sigF gene encodes a stationary phase/stress response sigma factor. This pattern of induction is similar to that of the *B. subtilis* sigB gene.

*M. tuberculosis* can survive for relatively long periods in expectorated sputum. Survival outside the human host requires adaptation to oxidative stress, low nutrient levels, and low temperature. The biochemical and genetic alterations permitting the organism to survive under these conditions are unknown. All of these conditions, in particular cold shock, induce *M. tuberculosis* sigF transcription. It is possible that sigF is important for survival outside of the host. *M. tuberculosis* sigF is involved in the adaptation of the organism during latent infection. The observation that *M. tuberculosis* has a sigma factor closely related to sporulation sigmas from *S. coelicolor* and *B. subtilis* is intriguing since tubercle bacilli are classically described as non-sporulating bacilli. Both the *B. subtilis* sigB and sigF genes are transcribed as parts of polycistronic messages containing post-translational regulatory genes (24–28). The sigB operon encodes three other genes (rsbV, rsbW, and rsbX) which control SigB activation. The *B. subtilis* sigF operon encodes two other genes encoding an anti-sigma factor (SpoIIAB) and an anti-anti-sigma factor (SpoIIAA). The *S. coelicolor* sigF gene appears to be monocistronic (17). Molecular genetic studies using the *M. tuberculosis* sigF gene may help address the question of whether tubercle bacilli enter a spore-like state during persistent infection.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

References

1. Smith, P. G., and A. R. Moss. 1994. Epidemiology of tuberculosis. In B. R. Bloom (ed.) Tuberculosis: Pathogenesis, Protection, and Control. ASM Press, Washington, D. C., pp.47–59.

2. Bloom, B. R. and C.J.L. Murray. 1992. Tuberculosis: commentary on a reemergent killer. Science 257: 1055–1064.

3. Gedde-Dahl, T. 1952. Tuberculous infection in the light of tuberculin matriculation. Am. J. Hyg. 56:139–214.

4. Sudre, P., G. ten Dam, A. Kochi. 1992. Tuberculosis: a global overview of the situation today. Bull. WHO 70:149–159.

5. Wayne, L. G. 1994. Dormancy of Mycobacterium tuberculosis and latency of disease. Eur. J. Clin. Microbiol. Infect. Dis. 13:908–914.

6. Khomenko, A. G. 1980. L-transformation of the mycobacterial population in the process of treating patients with newly detected destructive pulmonary tuberculosis. Probl. Tuberk. 2:18–23.

7. Werner, G. H. 1954. Filterable forms of *Mycobacterium tuberculosis*. Am. Rev. Tuberc. 69:473–474.

8. Ausubel, F. M., Brent, R., Kingston, R. E., Moore, D. D., Seidman, J. G., Smith, J. A., Struhl, K. (1994) Current Protocols in Molecular Biology (John Wiley and Sons, Inc.), pp. 1.8.4–1.8.8.

9. Sambrook, J., Fritsch, E. F., Maniafis, T. (1989) Molecular Cloning: A Laboratory Manual (Cold Spring Harbor Lab. Press, Plainview, N.Y.), pp. 9.31–9.57.

10. Wayne, L. G. (1976) Am. Rev. Resp. Dis. 114, 807–811.

11. Lonetto, M., Gribskov, M., Gross, C. A. (1992) J. Bacteriol. 1764, 3843–3849.

12. Gross, C. A., Lonetto, M., Losick, R. (1992) in Transcriptional Regulation, eds. McKnight, S. L. & Yamamoto K. R. (Cold Spring Harbor Lab. Press, Plainview, N.Y.), Vol. 1, pp. 129–176.

13. Predich, M., Doukhan, L., Nair, G., Smith, I. (1995) Mol. Microbiol. 15, 355–366.

14. Kempsell, K. E., Ji, Y. E., Estrada, I. C., Colston, M. L, Cox, R. A. (1992) J. Gen. Microbiol. 138, 1717–1727.

15. Honore, N., Bergh, S., Chanteau, S., Doucet-Populaire, F., Eiglmeier, K., Garnier, T., Georges, G., Launois, P., Limpaiboon, T., Newton, S., Niang, K., del Portillo, P., Ramesh, G. R., Reddi, P., Ridel, P. R., Sittisombut, N., Wu-Hunter, S., Cole, S. T. (1993) Mol. Microbial. 7, 207–214.

16. Tanaka, K., Shiina, T., Takahashi, H. (1988) Science 242, 1040–1042.

17. Potuckova, L., Kelemen, G. H., Findlay, K. C., Lonetto, M. A., Buttner, M. J., Kormanec, J. (1995) Mol. Microbiol. 17, 37–48.

18. Gholamhoseinian, A., Piggot, P. J. (1989) *J. Bacteriol.* 171, 5747–5749.

19. Margolis, P., Driks, A., Losick, R. (1991) *Science* 254, 562–565.

20. Benson, A. K., Haldenwang, W. G. (1993) *J. Bacteriol.* 175, 2347–2356.

21. Boylan, S. A., Redfield, A. R., Brody, M. S., Price, C. W. (1993) *J. Bacteriol.* 175, 7931–7937.

22. Lonetto, M., Brown, K. L., Rudd, K., Buttner, M. J. (1994) *Proc. Natl. Acad. Sci. USA* 91, 7573–7577.

23. Haines, D. S., Gillespie, D. H. (1992) *Biotechniques* 12, 736–740.

24. Kalman S., Duncan, M., Thomas, S., Price, C. W. (1990) *J. Bacteriol.* 172, 5575–5585.

25. Benson, A. K., Haldenwang, W. G. (1993) *Proc. Natl. Acad. Sci. USA* 90, 2330–2334.

26. Schmidt, R., Margolis, P., Duncan, L., Coppolecchia, R., Moran C. P. Jr., Losick, R. (1990) *Proc. Natl. Acad. Sci. USA* 87, 9221–9225.

27. Min, K. T., Hilditch, C. M., Dieterich, B., Errington, J., Yudkin, M. D. (1993) *Cell* 74, 735–742.

28. Alper, S., Duncan, L., Losick, R. (1994) *Cell* 77, 195–205.

29. Schuler, G. D., Altschul, S. F., and Lipman, D. J. (1991). *Proteins Struct. Funct. Genet.* 9, 180–190.

30. Stanford, J. L. 1987. Much's granules revisited. Tubercle 68:241–242.

31. Csillag, A. 1964. The *Mycococcusform* of mycobacteria. *J. Gen. Microbiol.* 34: 341.

32. Khomenko, A. G. 1987. The variability of *Mycobacterium tuberculosis* in patients with cavitary pulmonary tuberculosis in the course of chemotherapy. Tuberde 68:243–253.

33. Barksdale, L., J. Convit, K.-S. Kim, M. E. de Pinardi. 1973. Spheroidal bodies and globi of human leprosy. Biochem. Biophys. Res. Comm. 54:290.

34. Chatterjee, B. R. 1976. A non-acid fast coccoid precursor-possible cultivable phase of *Mycobacterium leprae*. Leprosy in India 48:398.

35. Roek, G. A. W., and J. L. Stanford. 1992. Autoimmunity or slow bacterial infection? Immunol. Today 13:160–164.

36. Fidler, H. M., G. A. Rook, N. McL. Johnson, and J. McFadden. 1993. *Mycobacterium tuberculosis* DNA in tissue affected by sarcoidosis. BMJ 306:546–549.

37. Haldenwang, W. G. 1995 *Microbiol. Rev.* 59, 1–30.

38. Firestein, G. S., Gardner, S. M., Roeder, W. D. (1987) *Anal. Biochem.* 167, 381–386.

---

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2000 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycobacterium tuberculosis ( x i ) SEQUENCE DESCRIPTION: SEQ ID NO:1:

```
TGGTGGGGAT  GGCACGGCGC  CGGCTGGTTT  TTGTTGACGC  TGATGGTGCT  GACGCTCTGC      60
ATAGGCGTCC  CACCGATCGC  CGGCCCGGTC  ATGGCGCCGT  GAGCCGTCGG  CCAGGTCGGC     120
CGCGGTCAAC  AAATAAATGG  GTCAGATCCC  TCCACAACCC  GTTCGACGAG  TTCTACCGTT     180
GATGGTAGTG  CCTGGTAATG  GGCAGAAATG  GCGGAATAGG  ACGGAAACGG  AGGAGGCCAT     240
GGGCGACACC  TATCGTGACC  CCGTCGACCA  CTTGCGGACG  ACGCGGCCGC  TTGCCGGCGA     300
GTCGCTGATC  GACGTGGTGC  ATTGGCCTGG  GTATCTGTTG  ATTGTGGCCG  GTGTCGTCGG     360
CGGCGTCGGA  GCTCTTGCGG  CTTTCGGCAC  CGGACATCAC  GCCGAGGGCA  TGACCTTTGG     420
TGTGGTGGCG  ATTGTCGTCA  CAGTGGTTGG  TTTGGCGTGG  CTAGCGTTCG  AGCATCGGCG     480
GATACGCAAG  ATTGCCGATC  GCTGGTATAC  CGAACATCCC  GAAGTCCGGC  GGCAGCGGCT     540
GGCCGGCTAG  ACATCCTAGT  GCGGCTGGAA  ATCCCGGCAT  CGCGGGGTTT  CACCGGCAGC     600
```

-continued

```
TGCGAATGGG TATCACGGGT ACACCATGAT GAATCCCGAC CATGTTGCGT TAGATCCCCA      660
CTACCAGCAG GTCCGACCAT GACCGACCAG CTCGAAGACC AGACCCAAGG CGGGAGTACT      720
GTCGATCGAA GCTTGCCGGG AGGGTGCATG GCCGACTCGG ATTTACCCAC CAAGGGGCGC      780
CAACGCGGTG TCCGCGCCGT CGAGCTGAAC GTTGCTGCCC GCCTGGAGAA CCTGGCGCTG      840
CTGCGCACCC TGGTCGGCGC CATCGGCACC TTCGAGGACC TGGATTTCGA CGCCGTGGCC      900
GACCTGAGGT TGGCGGTGGA CGAGGTGTGC ACCCGGTTGA TTCGCTCGGC CTTGCCGGAT      960
GCCACCCTGC GCCTGGTGGT CGATCCNCGA AAAGACGAAG TTGTGGTGGA GGCTTCTGCT     1020
GCCTGCGACA CCCACGACGT GGTGGCACCG GGCAGCTTTA GCTGGCATGT CCTGACCGCG     1080
CTGGCCGACG ACGTCCAGAC CTTCCACGAC GGTCGCCAGC CCGATGTAGC CGGCAGTGTC     1140
TTCGGCATCA CGTTGACCGC CCGACGGGCG GCATCCAGCA GGTGACGGCG CGCGCTGCCG     1200
GCGGTTCTGC ATCGCGAGCT AACGAATACG CCGACGTTCC GGAGATGTTT CGCGAGCTGG     1260
TTGGTTTGCC TGCCGGCTCA CCGGAATTCC AGCGGCACCG GACAAGATC GTTCAGCGGT      1320
GCTTGCCGCT GGCCGATCAC ATCGCGCGGC GGTTCGAGGG TCGCGGCGAA CCGCGTGACG     1380
ACCTTATTCA GGTCGCGCGG GTCGGGCTGG TCAACGCCGC GGTTCGCTTC GACGTGAAGA     1440
CCGGGTCGGA CTTCGTCTCC TTCGCGGTTC CTACCATCAT GGGCGAGGTC CGACGACACT     1500
TCCGCGACAA CAGCTGGTCG GTCAAGGTTC CCCGGCGTCT CAAGGAACTG CATCTGCGGC     1560
TAGGTACCGC CACCGCCGAT TTGTCGCAGC GGCTCGGGCG GCGCCGTCG GCATCGGAGC      1620
TCGCCGCGGA GCTCGGGATG GACCGCGCTG AGGTTATCGA AGGTTTGCTG GCGGGTAGTT     1680
CCTACCACAC CTTGTCCATC GACAGCGGTG GCGGCAGCGA CGACGATGCC CGCGCAATCA     1740
CAGACACCCT GGGCGACGTG GATGCGGGTC TTGACCAGAT CGAGAATCGG GAGGTGCTTC     1800
GTCCGTTGCT CGAGGCGTTG SCCGAGCGGG AACGAACGGT CTTGGTGCTC AGGTTCTTCG     1860
ACTCGATGAC CCAAACGCAG ATCGCCGAGC GCGTCGGTAT CTCACAGATG CACGTGTCGC     1920
GGGTGCTGGC CAAGTCATTG GCACGGCTAC GGGATCAGTT GGAGTAGCCG CCGGGCTTAC     1980
TTGGATCTCG GCGRAGCACC                                                 2000
```

( 2 ) INFORMATION FOR SEQ ID NO:2:

( i ) SEQUENCE CHARACTERISTICS:
    ( A ) LENGTH: 261 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( A ) ORGANISM: Mycobacterium tuberculosis ( x i ) SEQUENCE DESCRIPTION: SEQ ID NO:2:

```
Met Thr Ala Arg Ala Ala Gly Gly Ser Ala Ser Arg Ala Asn Glu Tyr
1               5                   10                  15
Ala Asp Val Pro Glu Met Phe Arg Glu Leu Val Gly Leu Pro Ala Gly
                20                  25                  30
Ser Pro Glu Phe Gln Arg His Arg Asp Lys Ile Val Gln Arg Cys Leu
            35                  40                  45
Pro Leu Ala Asp His Ile Ala Arg Arg Phe Glu Gly Arg Gly Glu Pro
        50                  55                  60
Arg Asp Asp Leu Ile Gln Val Ala Arg Val Gly Leu Val Asn Ala Ala
65                  70                  75                  80
```

```
Val  Arg  Phe  Asp  Val  Lys  Thr  Gly  Ser  Asp  Phe  Val  Ser  Phe  Ala  Val
               85                      90                      95

Pro  Thr  Ile  Met  Gly  Glu  Val  Arg  Arg  His  Phe  Arg  Asp  Asn  Ser  Trp
              100                     105                    110

Ser  Val  Lys  Val  Pro  Arg  Arg  Leu  Lys  Glu  Leu  His  Leu  Arg  Leu  Gly
         115                      120                      125

Thr  Ala  Thr  Ala  Asp  Leu  Ser  Gln  Arg  Leu  Gly  Arg  Ala  Pro  Ser  Ala
     130                     135                     140

Ser  Glu  Leu  Ala  Ala  Glu  Leu  Gly  Met  Asp  Arg  Ala  Glu  Val  Ile  Glu
145                     150                      155                          160

Gly  Leu  Leu  Ala  Gly  Ser  Ser  Tyr  His  Thr  Leu  Ser  Ile  Asp  Ser  Gly
               165                      170                     175

Gly  Gly  Ser  Asp  Asp  Asp  Ala  Arg  Ala  Ile  Thr  Asp  Thr  Leu  Gly  Asp
               180                     185                    190

Val  Asp  Ala  Gly  Leu  Asp  Gln  Ile  Glu  Asn  Arg  Glu  Val  Leu  Arg  Pro
          195                     200                      205

Leu  Leu  Glu  Ala  Leu  Pro  Glu  Arg  Glu  Arg  Thr  Val  Leu  Val  Leu  Arg
     210                     215                      220

Phe  Phe  Asp  Ser  Met  Thr  Gln  Thr  Gln  Ile  Ala  Glu  Arg  Val  Gly  Ile
225                     230                      235                          240

Ser  Gln  Met  His  Val  Ser  Arg  Val  Leu  Ala  Lys  Ser  Leu  Ala  Arg  Leu
                    245                     250                     255

Arg  Asp  Gln  Leu  Glu
               260
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mycobacterium tuberculosis ( x i ) SEQUENCE DESCRIPTION: SEQ ID NO:3:

```
AACCTGCGHC TSGTSGTC                                                          18
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

```
Asn  Leu  Arg  Leu  Val  Val
1                    5
```

( 2 ) INFORMATION FOR SEQ ID NO:5:

( i ) SEQUENCE CHARACTERISTICS:
        ( A ) LENGTH: 24 base pairs ( B ) TYPE: nucleic acid
                            ( C ) STRANDEDNESS: single
                            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
                            ( A ) ORGANISM: Mycobacterium tuberculosis ( x i ) SEQUENCE DESCRIPTION: SEQ ID NO:5:

CTGNCGKATC CACCASGTSG CRTA                                                                                      24

( 2 ) INFORMATION FOR SEQ ID NO:6:

( i ) SEQUENCE CHARACTERISTICS:
                            ( A ) LENGTH: 8 amino acids
                            ( B ) TYPE: amino acid
                            ( D ) TOPOLOGY: linear ( i i ) MOLECULE TYPE: peptide ( v i ) ORIGINAL SOURCE:
                            ( A ) ORGANISM: Mycobacterium tuberculosis ( x i ) SEQUENCE DESCRIPTION: SEQ ID NO:6:

Tyr  Ala  Thr  Trp  Trp  Ile  Arg  Gln
    1                   5

( 2 ) INFORMATION FOR SEQ ID NO:7:

( i ) SEQUENCE CHARACTERISTICS:
                            ( A ) LENGTH: 287 amino acids
                            ( B ) TYPE: amino acid
                            ( D ) TOPOLOGY: linear ( i i ) MOLECULE TYPE: protein ( i i i ) HYPOTHETICAL: NO ( v i ) ORIGINAL SOURCE:
                            ( A ) ORGANISM: Streptomyces coelicolor ( x i ) SEQUENCE DESCRIPTION: SEQ ID NO:7:

Met  Pro  Ala  Ser  Thr  Ala  Pro  Gln  Ala  Pro  Pro  Ala  Pro  Pro  Ala  Gln
    1                   5                   10                  15

Ala  Gln  Ala  Gln  Ala  Pro  Ala  Gln  Ala  Gln  Glu  Ala  Pro  Ala  Pro  Gln
                        20                  25                  30

Arg  Ser  Arg  Gly  Ala  Asp  Thr  Arg  Ala  Leu  Thr  Gln  Val  Leu  Phe  Gly
                   35                       40                  45

Glu  Leu  Lys  Gly  Leu  Ala  Pro  Gly  Thr  Pro  Glu  His  Asp  Arg  Val  Arg
              50                       55                  60

Ala  Ala  Leu  Ile  Glu  Ala  Asn  Leu  Pro  Leu  Val  Arg  Tyr  Ala  Ala  Ala
    65                       70                       75                       80

Arg  Phe  Arg  Ser  Arg  Asn  Glu  Pro  Met  Glu  Asp  Val  Val  Gln  Val  Gly
                        85                       90                       95

Thr  Ile  Gly  Leu  Ile  Asn  Ala  Ile  Asp  Arg  Phe  Asp  Pro  Glu  Arg  Gly
                   100                      105                      110

Val  Gln  Phe  Pro  Thr  Phe  Ala  Met  Pro  Thr  Val  Val  Gly  Glu  Ile  Lys
                   115                      120                      125

Arg  Tyr  Phe  Arg  Asp  Asn  Val  Arg  Thr  Val  His  Val  Pro  Arg  Arg  Leu
              130                      135                      140

His  Glu  Leu  Trp  Val  Gln  Val  Asn  Ser  Ala  Thr  Glu  Asp  Leu  Thr  Thr

```
      145                  150                      155                      160
Ala Phe Gly Arg Ser Pro Thr Thr Ala Glu Ile Ala Glu Arg Leu Arg
                165                  170                  175

Ile Thr Glu Glu Glu Val Leu Ser Cys Ile Glu Ala Gly Arg Ser Tyr
                180                  185                  190

His Ala Thr Ser Leu Glu Ala Ala Gln Glu Gly Asp Gly Leu Pro Gly
            195                  200                  205

Leu Leu Asp Arg Leu Gly Tyr Glu Asp Pro Ala Leu Asp Gly Val Glu
        210                  215                  220

His Arg Asp Leu Val Arg His Leu Leu Val Gln Leu Pro Glu Arg Glu
225                      230                  235                  240

Gln Arg Ile Leu Leu Leu Arg Tyr Tyr Ser Asn Leu Thr Gln Ser Gln
                245                  250                  255

Ile Ser Ala Glu Leu Gly Val Ser Gln Met His Val Ser Arg Leu Leu
                260                  265                  270

Ala Arg Ser Phe Gln Arg Leu Arg Ser Ala Asn Arg Ile Asp Ala
            275                  280                  285
```

( 2 ) INFORMATION FOR SEQ ID NO:8:

( i ) SEQUENCE CHARACTERISTICS:
       ( A ) LENGTH: 255 amino acids
       ( B ) TYPE: amino acid
       ( D ) TOPOLOGY: linear ( i i ) MOLECULE TYPE: protein ( i i i ) HYPOTHETICAL: NO ( v i ) ORIGINAL SOURCE:
       ( A ) ORGANISM: Bacillus subtilis ( x i ) SEQUENCE DESCRIPTION: SEQ ID NO:8:

```
Met Asp Val Glu Val Lys Lys Asn Gly Lys Asn Ala Gln Leu Lys Asp
1               5                   10                  15

His Glu Val Lys Glu Leu Ile Lys Gln Ser Gln Asn Gly Asp Gln Gln
                20                  25                  30

Ala Arg Asp Leu Leu Ile Glu Lys Asn Met Arg Leu Val Trp Ser Val
            35                  40                  45

Val Gln Arg Phe Leu Asn Arg Gly Tyr Glu Pro Asp Asp Leu Phe Gln
        50                  55                  60

Ile Gly Cys Ile Gly Leu Leu Lys Ser Val Asp Lys Phe Asp Leu Thr
65                  70                  75                  80

Tyr Asp Val Arg Phe Ser Thr Tyr Ala Val Pro Met Ile Ile Gly Glu
                85                  90                  95

Ile Gln Arg Phe Ile Arg Asp Asp Gly Thr Val Lys Val Ser Arg Ser
                100                 105                 110

Leu Lys Glu Leu Gly Asn Lys Ile Arg Arg Ala Lys Asp Glu Leu Ser
            115                 120                 125

Lys Thr Leu Gly Arg Val Pro Thr Val Gln Glu Ile Ala Asp His Leu
        130                 135                 140

Glu Ile Glu Ala Glu Asp Val Val Leu Ala Gln Glu Ala Val Arg Ala
145                 150                 155                 160

Pro Ser Ser Ile His Glu Thr Val Tyr Glu Asn Asp Gly Asp Pro Ile
                165                 170                 175

Thr Leu Leu Asp Gln Ile Ala Asp Asn Ser Glu Glu Lys Trp Phe Asp
            180                 185                 190

Lys Ile Ala Leu Lys Glu Ala Ile Ser Asp Leu Glu Glu Arg Glu Lys
```

```
                         195                      200                          205
       Leu  Ile  Val  Tyr  Leu  Arg  Tyr  Tyr  Lys  Asp  Gln  Thr  Gln  Ser  Glu  Val
            210                      215                      220

Ala  Glu  Arg  Leu  Gly  Ile  Ser  Gln  Val  Gln  Val  Ser  Arg  Leu  Glu  Lys
       225                      230                      235                      240

Lys  Ile  Leu  Lys  Gln  Ile  Lys  Val  Gln  Met  Asp  His  Thr  Asp  Gly
                           245                      250                      255
```

( 2 ) INFORMATION FOR SEQ ID NO:9:

( i ) SEQUENCE CHARACTERISTICS:
      ( A ) LENGTH: 262 amino acids
      ( B ) TYPE: amino acid
      ( D ) TOPOLOGY: linear ( i i ) MOLECULE TYPE: protein ( i i i ) HYPOTHETICAL: NO ( v i ) ORIGINAL SOURCE:
      ( A ) ORGANISM: Bacillus subtilis ( x i ) SEQUENCE DESCRIPTION: SEQ ID NO:9:

```
       Met  Thr  Gln  Pro  Ser  Lys  Thr  Thr  Lys  Leu  Thr  Lys  Asp  Glu  Val  Asp
       1                   5                        10                       15

Arg  Leu  Ile  Ser  Asp  Tyr  Gln  Thr  Lys  Gln  Asp  Glu  Gln  Ala  Gln  Glu
                           20                       25                       30

Thr  Leu  Val  Arg  Val  Tyr  Thr  Asn  Leu  Val  Asp  Met  Leu  Ala  Lys  Lys
                      35                       40                       45

Tyr  Ser  Lys  Gly  Lys  Ser  Phe  His  Glu  Asp  Leu  Arg  Gln  Val  Gly  Met
            50                       55                       60

Ile  Gly  Leu  Leu  Gly  Ala  Ile  Lys  Arg  Tyr  Asp  Pro  Val  Val  Gly  Lys
       65                       70                       75                       80

Ser  Phe  Glu  Ala  Phe  Ala  Ile  Pro  Thr  Ile  Ile  Gly  Glu  Ile  Lys  Arg
                           85                       90                       95

Phe  Leu  Arg  Asp  Lys  Thr  Trp  Ser  Val  His  Val  Pro  Arg  Arg  Ile  Lys
                      100                      105                      110

Glu  Leu  Gly  Pro  Arg  Ile  Lys  Met  Ala  Val  Asp  Gln  Leu  Thr  Thr  Glu
                 115                      120                      125

Thr  Gln  Arg  Ser  Pro  Lys  Val  Glu  Glu  Ile  Ala  Glu  Phe  Leu  Asp  Val
            130                      135                      140

Ser  Glu  Glu  Glu  Val  Leu  Glu  Thr  Met  Glu  Met  Gly  Lys  Ser  Tyr  Gln
       145                      150                      155                      160

Ala  Leu  Ser  Val  Asp  His  Ser  Ile  Glu  Ala  Asp  Ser  Asp  Gly  Ser  Thr
                           165                      170                      175

Val  Thr  Ile  Leu  Asp  Ile  Val  Gly  Ser  Gln  Glu  Asp  Gly  Tyr  Glu  Arg
                      180                      185                      190

Val  Asn  Gln  Gln  Leu  Met  Leu  Gln  Ser  Val  Leu  His  Val  Leu  Ser  Asp
                 195                      200                      205

Arg  Glu  Lys  Gln  Ile  Ile  Asp  Leu  Thr  Tyr  Ile  Gln  Asn  Lys  Ser  Gln
            210                      215                      220

Lys  Glu  Thr  Gly  Asp  Ile  Leu  Gly  Ile  Ser  Gln  Met  His  Val  Ser  Arg
       225                      230                      235                      240

Leu  Gln  Arg  Lys  Ala  Val  Lys  Lys  Leu  Arg  Glu  Ala  Leu  Ile  Glu  Asp
                           245                      250                      255

Pro  Ser  Met  Glu  Leu  Met
                      260
```

We claim:

1. An isolated and purified subgenomic DNA segment consisting of the nucleotide sequence shown in SEQ ID NO: 1.

2. An isolated and purified subgenomic DNA segment encoding a *M. tuberculosis* sigma factor sigF as shown in SEQ ID NO:2.

3. A vector comprising the DNA segment of claim 2.

4. The vector of claim 3 further comprising expression control sequences, whereby said DNA is expressed in a host cell transformed by the vector.

5. A host cell transformed with the DNA segment of claim 2.

6. A host cell transformed with the vector of claim 3.

* * * * *